(12) United States Patent
De Soto-Burt et al.

(10) Patent No.: US 9,120,609 B2
(45) Date of Patent: Sep. 1, 2015

(54) WRAPPER FOR PERSONAL CARE ARTICLE

(71) Applicant: The Procter & Gamble Company, Cincinnati, OH (US)

(72) Inventors: Widalys Luz De Soto-Burt, Loveland, OH (US); Gregory James Wilson, New Gloucester, ME (US)

(73) Assignee: The Procter & Gamble Company, Cincinnati, OH (US)

( * ) Notice: Subject to any disclaimer, the term of this patent is extended or adjusted under 35 U.S.C. 154(b) by 104 days.

(21) Appl. No.: 14/060,847

(22) Filed: Oct. 23, 2013

(65) Prior Publication Data
US 2015/0108207 A1 Apr. 23, 2015

(51) Int. Cl.
*B65D 75/58* (2006.01)
*A61F 13/551* (2006.01)

(52) U.S. Cl.
CPC .......... *B65D 75/5827* (2013.01); *A61F 13/551* (2013.01); *A61F 13/55175* (2013.01); *B65D 75/5816* (2013.01)

(58) Field of Classification Search
CPC ................ A61F 15/001; A61F 15/003; A61F 2013/00897; A61F 13/551; A61F 13/55175; B65D 75/5805; B65D 75/5827; B65D 75/5833; B65D 75/5844; B65D 75/5816

USPC ................ 206/440, 441; 229/87.05; 383/207; 604/385.02
See application file for complete search history.

(56) References Cited

U.S. PATENT DOCUMENTS

| | | | |
|---|---|---|---|
| 6,340,088 B1 | 1/2002 | Mouri et al. | |
| 6,955,665 B2 | 10/2005 | Domeier et al. | |
| 8,070,359 B2 * | 12/2011 | Taheri | 383/207 |
| 8,286,793 B2 * | 10/2012 | Kondo et al. | 206/440 |
| 8,302,844 B2 * | 11/2012 | McConnell et al. | 229/87.05 |
| 8,317,765 B2 | 11/2012 | Loyd et al. | |
| 8,419,700 B2 * | 4/2013 | Fung et al. | 604/385.02 |
| 8,740,458 B2 * | 6/2014 | Edwards et al. | 383/207 |
| 2003/0004089 A1 | 1/2003 | Huber et al. | |
| 2004/0134822 A1 | 7/2004 | Otsubo | |
| 2007/0081745 A1 * | 4/2007 | Tetenborg et al. | 383/207 |
| 2010/0226598 A1 * | 9/2010 | Stoeppelmann | 383/207 |
| 2012/0213456 A1 * | 8/2012 | Sugiyama et al. | 383/207 |
| 2014/0174042 A1 | 6/2014 | Ezaki et al. | |

OTHER PUBLICATIONS

PCT International Search Report, mailed Dec. 22, 2014, 104 pages.

* cited by examiner

*Primary Examiner* — Bryon Gehman
(74) *Attorney, Agent, or Firm* — Andrew J. Hagerty

(57) ABSTRACT

Wrappers for personal care articles are described. The wrappers have a unique line of weakness that facilitates both high-speed manufacture and the consumer use experience.

21 Claims, 4 Drawing Sheets

WRAPPER FOR PERSONAL CARE ARTICLE

FIELD OF THE INVENTION

The present invention is directed to wrappers for personal care articles. The wrappers comprise a line of weakness to facilitate their opening.

BACKGROUND OF THE INVENTION

A personal care article's wrapper can be an important element for consumers when selecting which article brand they want to purchase. Some of the factors that consumers may consider include how quiet or loud the wrappers are when transported and handled, the opening feature, the ability to use an opened wrapper for used article disposal, and the integrity of the wrapper for holding up during storage and transport prior to using the personal care article.

The wrapper opening feature can be especially important because it can directly impact the overall usage experience. One traditional manufacturing process forms wrappers by folding a substrate over on itself and sealing the remaining three edges. An example of the resulting wrapper is shown in FIG. 1, wherein wrapper 10 includes a folded edge 12, a front substrate portion 13, a back substrate portion 14, and three sealed edges 15a, 15b, and 15c. High speed processes for making these types of wrappers generally require some tolerance for matching the front and back of the substrate, leading to some level of material front-to-back offsetting—see, for example, offset 11 in FIG. 1.

A line of weakness (e.g., a perforated line) can be employed as a means to open the sealed wrapper. The line of weakness in some commercially-available products is completely horizontal, such as that shown in FIG. 1 (the line of weakness is element 16 in the figure). The downside of a completely horizontal line of weakness is that it provides the smallest opening for removing a contained article and for reinserting a used article. Thus, angling the line of weakness can create a larger opening. But the front-to-back offsetting, as discussed above, can result in a wrapper where the lines of weakness on the front and back portions (elements 16a and 16b, respectively) do not line up, as is shown in FIG. 2, which can cause an undesirable opening experience for the consumer. Embodiments of the present invention address these two shortcomings.

SUMMARY OF THE INVENTION

In accordance with one embodiment, there has now been provided a wrapper for a personal care article, comprising a longitudinal axis, a transverse axis, a first sheet and a second sheet adjacent to and joined to the first sheet in a manner to create an interior volume capable of containing a personal care article. The wrapper includes a first wrapper edge that is substantially orthogonal to the transverse axis, and a second wrapper edge spaced apart from the first wrapper edge. The first sheet includes a first line of weakness and the second sheet includes a second line of weakness. Each of the first line of weakness and the second line of weakness comprises a first portion proximate the first wrapper edge that is angled more than 0 degrees but less than 5 degrees with respect to a reference line that is parallel to the transverse axis. And each of the first and second lines of weakness further comprises a second portion distal to the first wrapper edge that is angled to a greater extent than the first portion but less than 90 degrees with respect to the reference line.

In accordance with another embodiment, there has now been provided a wrapper for a personal care article, comprising a longitudinal axis, a transverse axis, a first sheet and a second sheet adjacent to and joined to the first sheet in a manner to create an interior volume capable of containing a personal care article. The wrapper includes a first wrapper edge that is substantially orthogonal to the transverse axis, and a second wrapper edge spaced apart from the first wrapper edge. The first sheet includes a first line of weakness and the second sheet includes a second line of weakness. Each of the first line of weakness and the second line of weakness comprises a first portion proximate the first wrapper edge, the first portion comprising a first angle with respect to a reference line that is parallel to the transverse axis, and a plurality of first cut regions and first non-cut regions therebetween. Each of the first line of weakness and the second line of weakness further comprises a second portion distal to the first wrapper edge, the second portion comprising a second angle with respect to the reference line that is different from the first angle, and a plurality of second cut regions and second non-cut regions therebetween. A length of at least some of the first cut regions is different from a length of at least some of the second cut regions and/or a length of at least some of the first non-cut regions is different from a length of at least some of the second non-cut regions.

In accordance with yet another embodiment, there has now been provided a wrapper for a personal care article, comprising a first sheet and a second sheet adjacent to and joined to the first sheet in a manner to create an interior volume capable of containing a personal care article. The wrapper includes a first wrapper edge that is substantially orthogonal to a transverse axis, and a second wrapper edge spaced apart from the first wrapper edge. The first sheet includes a first line of weakness and the second sheet includes a second line of weakness. Each of the first line of weakness and the second line of weakness comprises a first portion proximate the first wrapper edge, the first portion comprising a first length, and a plurality of first cut regions and first non-cut regions therebetween. Each of the first line of weakness and the second line of weakness further comprises a second portion distal to the first wrapper edge, the second portion comprising a second length that is different from the first length, and a plurality of second cut regions and second non-cut regions therebetween. A length of at least some of the first cut regions is different from a length of at least some of the second cut regions and/or a length of at least some of the first non-cut regions is different from a length of at least some of the second non-cut regions.

In accordance with another embodiment, there has now been provided a wrapper for a personal care article, comprising a first sheet and a second sheet adjacent to and joined to the first sheet in a manner to create an interior volume capable of containing a personal care article. The wrapper includes a first wrapper edge and a second wrapper edge spaced apart from the first wrapper edge. The first sheet includes a first line of weakness and the second sheet includes a second line of weakness. Each of the first line of weakness and the second line of weakness comprising a first portion that is proximate the first wrapper edge and second portion that is distal to the first wrapper edge. The first portion includes a first length, a first angle, and a plurality of first cut regions and first non-cut regions therebetween. The first length is between 0.5 and 15 millimeters. The second portion includes a second length, a second angle, and a plurality of second cut regions and second non-cut regions therebetween. The second length is longer than the first length. And the first angle differs from the second angle by 10 to 75 degrees.

BRIEF DESCRIPTION OF THE DRAWINGS

The following detailed description of specific embodiments of the present invention can be best understood when read in conjunction with the drawings enclosed herewith.

Figure 1:
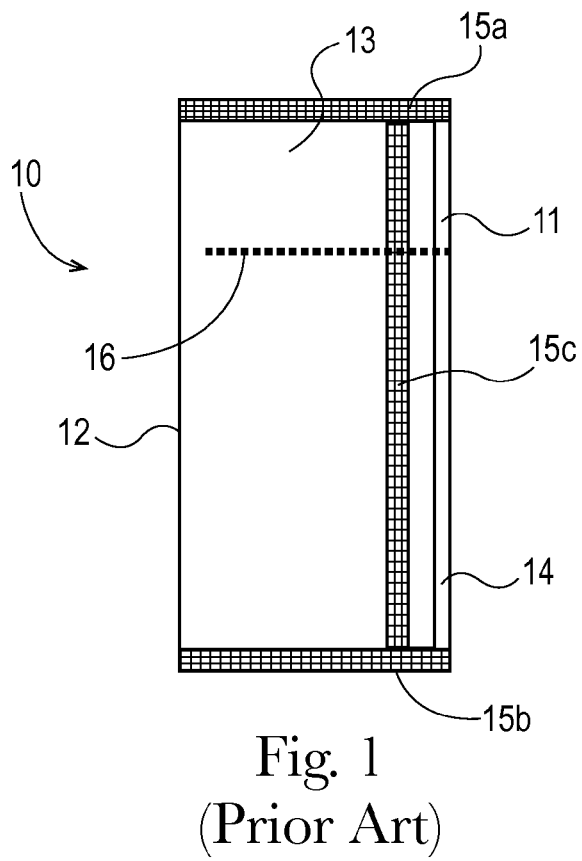
FIG. 1 is a side view of a wrapper discussed in the Background Section.
Figure 2:
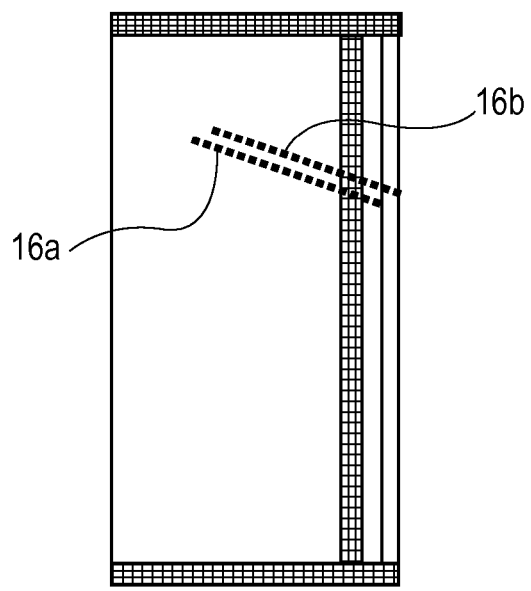
FIG. 2 is a side view of another wrapper discussed in the Background Section.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

The present invention is directed to wrappers for personal care articles. The wrappers generally at least partially enclose the article prior to the article's use, and in some embodiments, the wrappers may be configured to receive a used article for disposal purposes. The type of personal care articles the wrapper can contain is not limited. Some examples of personal care articles suitable for the wrappers of the present invention are absorbent articles such as diapers, sanitary napkins, pads, pantiliners, adult incontinence products (pads, briefs, and pessaries), tampons, wipes, and any other article that is useful in managing and/or controlling the discharge of bodily fluids. The personal care articles can be disposable, semi-durable, or durable. As used herein, the term "disposable" means single use.

The wrappers can be constructed from numerous materials, including, for example, polymeric films, fibrous materials (including nonwovens and wovens), paper, card stock, and combinations thereof. In one preferred embodiment, the wrappers are constructed from flexible, polymeric films. The polymeric films may be based on polyethylene, polypropylene, polyester, nylon, polyvinyl alcohol, or blends of the same. One exemplary material is a 32 gauge polyethylene film. The materials may be a single layer or more than one layer. The wrappers can be formed from a single feedstock of material that is manipulated into a container, such as by folding, or can be formed from multiple feedstocks that are joined together to ultimately form the finished wrapper.

The wrappers generally at least partially enclose the personal care article, and preferably, substantially completely enclose the article. As noted above, in some embodiments, the wrapper is configured to accept a used article to facilitate disposal of the same.

Various opening mechanisms can be employed. A line of weakness is one such opening mechanism. The line of weakness can take many forms, including, but not limited to, a perforated line, a scored line, and an embossed line. The line of weakness can have a constant strength property or varying strength properties along its length. For example, a scored line can have one depth and/or width, or these dimensions can vary along the length of the scored line. Likewise, the dimensions of cut regions and non-cut regions therebetween of a perforated line can be constant or variable. Varying the tear strength of a line of weakness can accomplish multiple design goals. For example, it can be desirable to have a low tear strength at the beginning of a line of weakness to help start the opening process and then have a relatively higher tear strength further down the line of weakness to indicate the wrapper is opened sufficiently or to help mitigate separating the wrapper into multiple pieces.

Figure 3:
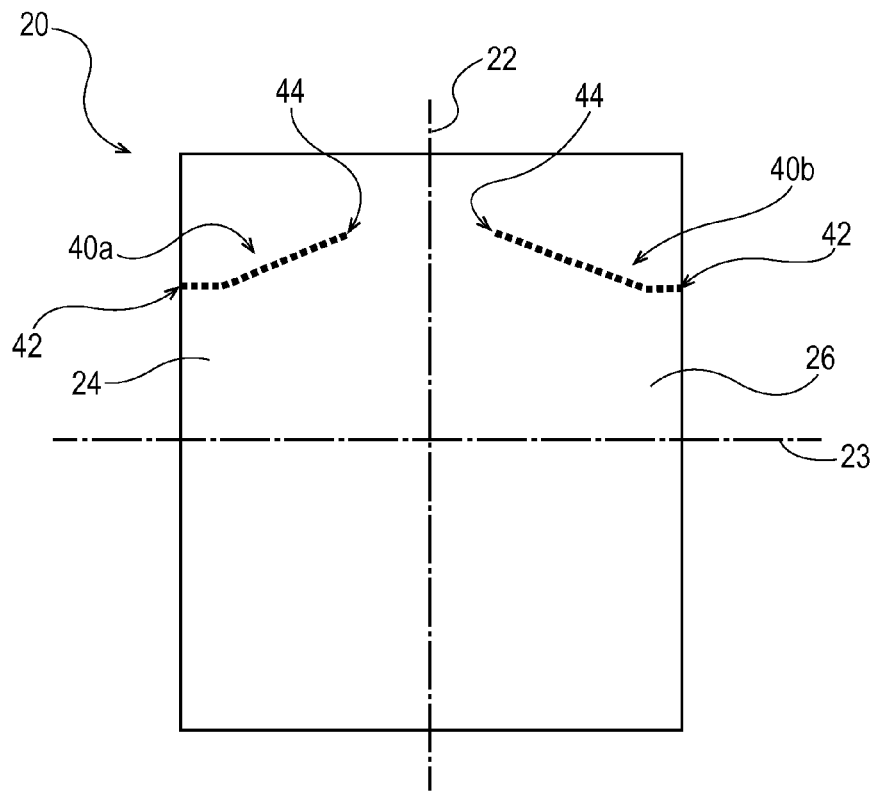
FIG. 3 is a side view of a wrapper substrate embodiment of the present invention.
Figure 4:
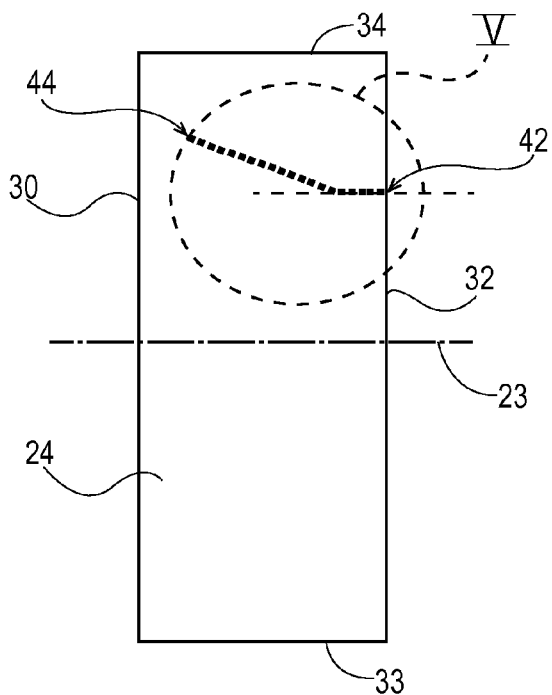
FIG. 4 is a side view of the wrapper substrate of FIG. 3 that has been folded in half.

Referring again to the drawings and in particular to FIGS. 3 and 4, a wrapper substrate 20 is shown having a longitudinal axis 22 and a transverse axis 23 that is orthogonal to longitudinal axis 22. Substrate 20 includes a first portion 24 and a second adjacent portion 26. During manufacture, substrate 20 is folded about longitudinal axis 22 substantially in half such that first portion 24 and second portion 26 are in a facing relationship, as can be seen in FIG. 4. The resulting intermediate structure has a folded edge 30 and three free edges 32, 33, and 34. Before, during, and/or after placing a personal care article between first portion 24 and second portion 26, the individual free edges 32, 33, and 34 can be at least partially sealed. The method of sealing is not critical to the present invention, with exemplary modes including heat sealing, heat and pressure sealing, adhesive sealing, ultrasonic sealing, and the like.

As shown in FIGS. 3 and 4, wrappers of the present invention can be made from a single material feedstock that is folded or otherwise manipulated, wherein first portion 24 defines a wrapper first sheet and second portion 26 defines a wrapper second sheet that is in facing relationship with the first sheet. In alternative embodiments, wrappers of the present invention can be made from two or more material feedstocks that are joined together.

Two lines of weakness in the form of perforated lines 40a, 40b are included on substrate 20. Each of perforated lines 40a and 40b has a first end 42 and a second end 44. As shown in FIG. 4 first end 42 is proximate edge 32 of the substrate and is intended to serve as the starting point for opening a finished wrapper. Second end 44 does not extend all the way to edge 30 to help prevent separation of the wrapper into multiple pieces during the opening process. In alternative embodiments second end 44 can extend essentially to edge 30 with a design choice that the wrapper is intended to separate into multiple pieces. One should appreciate that even with a design such as that shown in FIGS. 3 and 4, a consumer may inadvertently start the opening process from edge 30 and/or separate the wrapper into two pieces.

Figure 5:
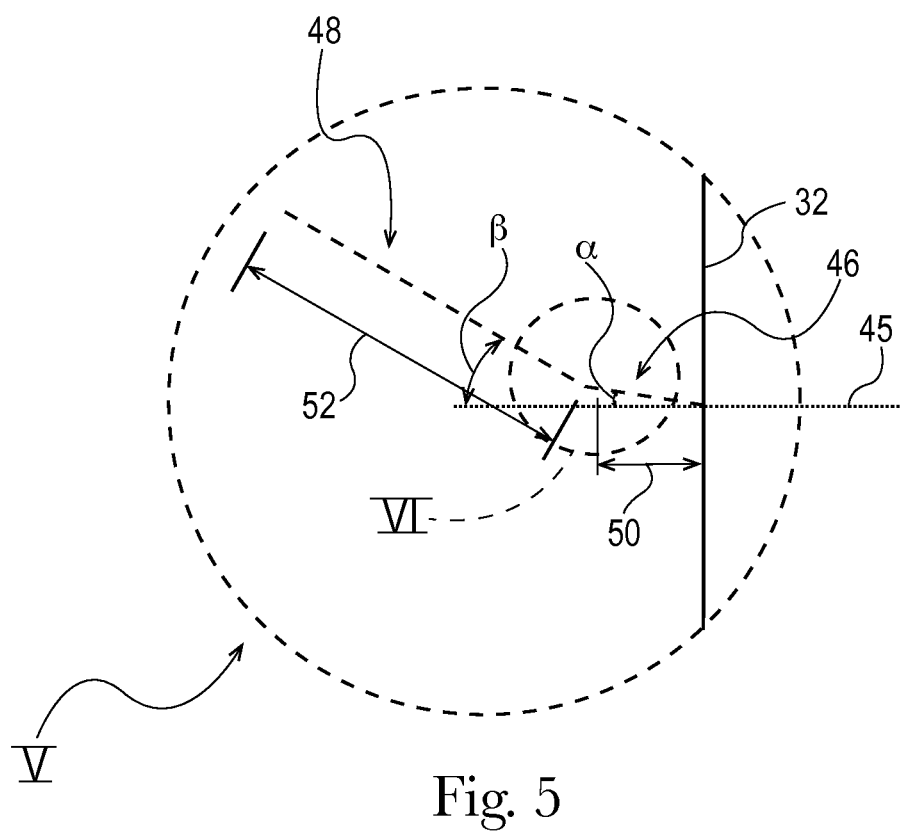
FIG. 5 is an enlarged view of section V shown in FIG. 4.

An enlarged view of perforated line 40a is shown in FIG. 5. Perforated line 40a includes a first portion 46 and a second portion 48. First portion 46 can have the same or a different length and/or the same or a different angle (with respect to a reference line 45 that is parallel to transverse axis 23) in comparison to second portion 48. In some embodiments, first portion 46 has an angle α of from greater than 0 degrees to less than about 10, 9, 8, 7, 6, 5, 4, 3, or 2 (+/−) degrees with respect to reference line 45. In other embodiments, first portion 46 has an angle α of 0 degrees. Although it is desirable to orient first portion 46 at a low angle to minimize the potential off-setting problem described in the Background Section, orienting it orthogonally to the edge can result in much faster tooling wear than if it has even a small angle. Second portion 48 has an angle β that is significantly greater than angle α to create a relatively large opening to aid in removing the contained personal care article and to facilitate receipt of a used article where desired. Angle β is less than 90 degrees with respect to reference line 45, and in some embodiments is between 15 and 75 degrees or 20 and 45 degrees. In another embodiment, angle α α is less than 5 degrees and angle β is greater than 20 degrees with respect to reference line 45. Other angles are also contemplated by the present invention. In some embodiments, angle α differs from angle β by more than 5 or 10 degrees but less than 90, 75, 60, 45, 30, or 20 degrees.

First portion 46 has a length 50 and second portion 48 has a length 52. Suitable lengths for length 50 include, but are not limited to 0.5, 1, 2, 3, 4, 5, 6, 7, 8, 9, and 15 millimeters. Suitable lengths for length 52 include, but are not limited to 20, 25, 30, 35 millimeters. As shown in FIG. 5, first portion length 50 is significantly shorter than second portion length 52. This can help address off-setting issues while providing a relatively large opening. One exemplary embodiment includes a length 50 of from about 0.5 to about 10 millimeters, and a length 52 that is longer than length 50. In some embodiments, the ratio of the second portion length 52 to the first portion length 50 is between 2:1 and 5:1. Other lengths and ratios are contemplated by the present invention. And in alternative embodiments, the first portion length and the second portion length can be essentially the same dimension. Although the line of weaknesses are shown as linear in the drawings, they can alternatively be curvilinear or a combination of linear and curvilinear. The length of a curvilinear line of weakness is measured by a straight line that passes through the two end points of the line.

Figure 6:
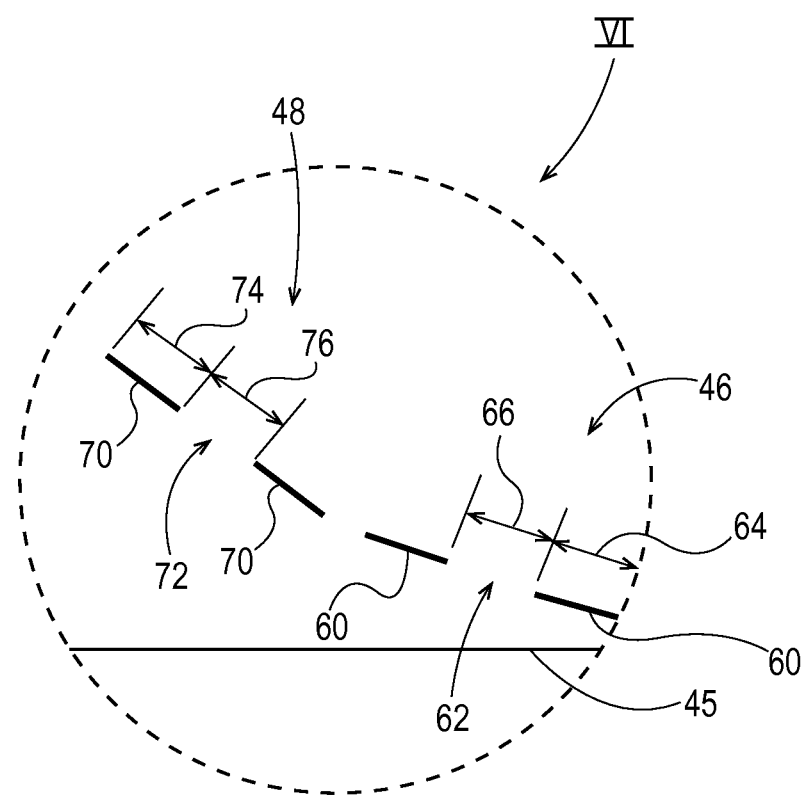
FIG. 6 is an enlarged view of section VI shown in FIG. 5.

FIG. 6 shows a partial enlarged view of perforated line 40a to facilitate description of the perforation cut regions and non-cut regions (or spaces) between adjacent cut regions. First portion 46 has a plurality of cut regions 60 and non-cut regions 62 therebetween. Cut regions 60 have a length 64; non-curt regions 62 have a length 66. Similarly, second portion 48 has a plurality of cut regions 70 and non-cut regions 72 therebetween. Cut regions 70 have a length 74; non-cut regions have a length 76. Exemplary cut lengths 64, 74 include 1.5 millimeters, 1.8 millimeters, and 2.0 millimeters. Exemplary non-cut lengths 66, 76 include 1 millimeter, 1.2 millimeters, and 1.5 millimeters. Other lengths are contemplated by the present invention.

In one embodiment, the length 64 of cut regions 60 is different from the length 74 of cut regions 70. For example, the length 64 of cut regions 60 can be longer than the length 74 of cut regions 70 to both facilitate an easy start to the opening process and deter separating the wrapper into multiple pieces. In another embodiment, the length 66 of non-cut regions 62 is different from the length 76 of non-cut regions 72. In yet another embodiment, both the length of the cut regions and the length of the non-cut regions differ when comparing first portion 46 and second portion 48. In some embodiments, at least one of the first perforated line 40a and the second perforated line 40b has a variable ratio of cut length to non-cut length along the length of the respective perforated line. It should be noted that while the dimensions of the cut regions and the non-cut regions have been discussed as being different from the first line of weakness portion to the second line of weakness portion, variations can occur within a single portion of the line of weakness.

The cut regions shown and described in conjunction with FIG. 6 are essentially elongated cuts having a major axis and a minor axis. Thus, a length dimension as described above generally is the largest chord dimension of the shown perforation geometry. However, the perforation geometry can vary within the spirit of the invention, including circular and square geometries. Thus, the maximum chord dimension can be substituted for length as it is discussed in relation to FIG. 6.

Perforated line 40b is not shown in FIGS. 5 and 6. It can have the same or different properties (including the lengths and angles of its first and second portions, and the perforation design) than those described above for perforated line 40a. The skilled artisan should readily appreciate that the lines of weakness can have more than two portions—for example, three, four, or five portions—with the different portions having similar or different properties.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 millimeters" is intended to mean "about 40 millimeters."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wrapper for a personal care article, comprising:
   a. a longitudinal axis;
   b. a transverse axis;
   c. a first sheet comprising a first line of weakness;
   d. a second sheet adjacent to and joined to the first sheet in a manner to create an interior volume capable of containing a personal care article, the second sheet comprising a second line of weakness;
   e. a first wrapper edge that is substantially orthogonal to the transverse axis; and
   f. a second wrapper edge spaced apart from the first wrapper edge;
   g. wherein each of the first line of weakness and the second line of weakness comprises a first portion proximate the first wrapper edge that is angled more than 0 degrees but less than 5 degrees with respect to a reference line that is parallel to the transverse axis; and
   h. wherein each of the first line of weakness and the second line of weakness comprises a second portion distal to the first wrapper edge that is angled to a greater extent than the first portion but less than 90 degrees with respect to the reference line.

2. The wrapper of claim 1, wherein each of the second portions has a terminal end that does not extend all the way to the second wrapper edge.

3. The wrapper of claim 1, wherein the second portion is angled at 15 degrees to 75 degrees with respect to the reference line.

4. The wrapper of claim 1, wherein the second portion is angled at 20 degrees to 45 degrees with respect to the reference line.

5. The wrapper of claim 1, wherein the first portion has a length that is shorter than that of the second portion.

6. The wrapper of claim 1, wherein a ratio of the length of the second portion to the length of the first portion is between 2:1 and 5:1.

7. The wrapper of claim 1, wherein each of the first line of weakness and the second line of weakness comprises a plurality of cut regions and non-cut regions therebetween, and wherein at least one of the first line of weakness and the second line of weakness comprises a variable ratio of a length of the cut regions to a length of the non-cut regions.

8. The wrapper of claim 7, wherein both of the first line of weakness and the second line of weakness comprise a variable ratio of a length of the cut regions to a length of the non-cut regions.

9. The wrapper of claim 1, wherein each of the first line of weakness and the second line of weakness comprises a plurality of cut regions and non-cut regions therebetween, wherein at least one of a cut length and a non-cut length of at least one of the first line of weakness and the second line of weakness is variable.

10. The wrapper of claim 1, wherein the first sheet and the second sheet are derived from a single sheet of material that is folded over on itself.

11. The wrapper of claim 1, wherein each of the first sheet and the second sheet comprises a flexible film.

12. The wrapper of claim 1, wherein the wrapper contains an intravaginal device.

13. A wrapper for a personal care article, comprising:
    a. a longitudinal axis;
    b. a transverse axis;
    c. a first sheet comprising a first line of weakness;
    d. a second sheet adjacent to and joined to the first sheet in a manner to create an interior volume capable of containing a personal care article, the second sheet comprising a second line of weakness;
    e. a first wrapper edge that is substantially orthogonal to the transverse axis; and
    f. a second wrapper edge spaced apart from the first wrapper edge;
    g. wherein each of the first line of weakness and the second line of weakness comprises a first portion proximate the first wrapper edge, the first portion comprising a first angle with respect to a reference line that is parallel to the transverse axis, and a plurality of first cut regions and first non-cut regions therebetween;
    h. wherein each of the first line of weakness and the second line of weakness comprises a second portion distal to the first wrapper edge, the second portion comprising a second angle with respect to the reference line that is different from the first angle, and a plurality of second cut regions and second non-cut regions therebetween; and
    i. wherein at least one of a length of at least some of the first cut regions is different from a length of at least some of the second cut regions, and a length of at least some of the first non-cut regions is different from a length of at least some of the second non-cut regions.

14. The wrapper of claim 13, wherein each of the second portions has a terminal end that does not extend all the way to the second wrapper edge.

15. The wrapper of claim 13, wherein the first angle differs from the second angle by 10 to 75 degrees.

16. The wrapper of claim 13, wherein the first angle is less than 5 degrees and the second angle is greater than 20 degrees.

17. The wrapper of claim 13, wherein the wrapper contains an intravaginal device.

18. A wrapper for a personal care article, comprising:
    a. a first sheet comprising a first line of weakness; and
    b. a second sheet adjacent to and joined to the first sheet in a manner to create an interior volume capable of containing a personal care article, the second sheet comprising a second line of weakness;
    c. a first wrapper edge; and
    d. a second wrapper edge spaced apart from the first wrapper edge;
    e. wherein each of the first line of weakness and the second line of weakness comprises a first portion proximate the first wrapper edge, the first portion comprising a first length, and a plurality of first cut regions and first non-cut regions therebetween;
    f. wherein each of the first line of weakness and the second line of weakness comprises a second portion distal to the first wrapper edge, the second portion comprising a second length that is different from the first length, and a plurality of second cut regions and second non-cut regions therebetween; and
    g. wherein at least one of a length of at least some of the first cut regions is different from a length of at least some of the second cut regions, and a length of at least some of the first non-cut regions is different from a length of at least some of the second non-cut regions.

19. The wrapper of claim 18, wherein the first length of the first portion is shorter than the second length of the second portion.

20. The wrapper of claim 18, wherein each of the second portions has a terminal end that does not extend all the way to the second wrapper edge.

21. A wrapper for a personal care article, comprising:
    a. a first sheet comprising a first line of weakness; and
    b. a second sheet adjacent to and joined to the first sheet in a manner to create an interior volume capable of containing a personal care article, the second sheet comprising a second line of weakness;
c. a first wrapper edge; and
d. a second wrapper edge spaced apart from the first wrapper edge;
e. wherein each of the first line of weakness and the second line of weakness comprises a first portion proximate the first wrapper edge, the first portion comprising a first length, a first angle, and a plurality of first cut regions and first non-cut regions therebetween;
f. wherein each of the first line of weakness and the second line of weakness comprises a second portion distal to the first wrapper edge, the second portion comprising a second length, a second angle, and a plurality of second cut regions and second non-cut regions therebetween; and
g. wherein the first length is between 0.5 and 15 millimeters;
h. wherein the second length is longer than the first length;
i. wherein the first angle differs from the second angle by 10 to 75 degrees.

* * * * *